US008335298B2

(12) United States Patent
Clawson

(10) Patent No.: US 8,335,298 B2
(45) Date of Patent: Dec. 18, 2012

(54) PANDEMIC DIAGNOSTIC AND INTERVENTION TOOL FOR EMERGENCY DISPATCH

(76) Inventor: Jeffrey J. Clawson, Salt Lake City, UT (US)

( * ) Notice: Subject to any disclaimer, the term of this patent is extended or adjusted under 35 U.S.C. 154(b) by 530 days.

(21) Appl. No.: 12/558,808

(22) Filed: Sep. 14, 2009

(65) Prior Publication Data
US 2011/0066002 A1    Mar. 17, 2011

(51) Int. Cl.
H04M 11/04 (2006.01)
(52) U.S. Cl. ....... 379/45; 379/38; 379/265.01; 600/300; 128/904; 128/905; 705/2
(58) Field of Classification Search ............ 379/45, 379/265.01, 38; 600/300; 128/903, 904, 128/905; 705/2
See application file for complete search history.

(56) References Cited

U.S. PATENT DOCUMENTS

| 3,799,147 A | 3/1974 | Adolph et al. |
| 4,130,881 A | 12/1978 | Haessler et al. |
| 4,164,320 A | 8/1979 | Irazoqui et al. |
| 4,237,344 A | 12/1980 | Moore |
| 4,290,114 A | 9/1981 | Sinay |
| 4,338,493 A | 7/1982 | Stenhuis et al. |
| 4,360,345 A | 11/1982 | Hon |
| 4,455,548 A | 6/1984 | Burnett |
| 4,489,387 A | 12/1984 | Lamb et al. |
| 4,731,725 A | 3/1988 | Suto et al. |
| 4,839,822 A | 6/1989 | Dormond et al. |
| 4,858,121 A | 8/1989 | Barber et al. |
| 4,865,549 A | 9/1989 | Sonsteby |
| 4,922,514 A | 5/1990 | Bergeron et al. |
| 4,926,495 A | 5/1990 | Comroe et al. |
| 4,945,476 A | 7/1990 | Bodick et al. |
| 4,967,754 A | 11/1990 | Rossi |
| 5,063,522 A | 11/1991 | Winters |
| 5,065,315 A | 11/1991 | Garcia |
| 5,072,383 A | 12/1991 | Brimm et al. |

(Continued)

FOREIGN PATENT DOCUMENTS
JP    2003109162 A    4/2003
(Continued)

OTHER PUBLICATIONS

International Search Report and Written Opinion mailed Jan. 19, 2011 in PCT Application No. PCT/US2010/043308, filed Jul. 27, 2010.

(Continued)

Primary Examiner — Gerald Gauthier
Assistant Examiner — Simon King
(74) Attorney, Agent, or Firm — John R. Thompson; Stoel Rives LLP

(57) ABSTRACT

A system and method to assist an emergency medical dispatcher in responding to emergency calls. A computer implemented emergency medical dispatch protocol includes interrogatories for a dispatcher to ask a caller to generate an appropriate response. A diagnostic tool is provided to aid the dispatcher in gathering symptom information for a patient who may be suffering from a pandemic illness, such as a severe respiratory infection like influenza. The diagnostic tool facilitates uniform and consistent gathering of symptom information relating to a pandemic outbreak. The information may be stored and/or processed for use in monitoring and/or tracking pandemic outbreaks. The diagnostic tool can be launched automatically by the emergency dispatch protocol, or manually by a dispatcher. The diagnostic tool presents a user interface that provides, among other things, instructions, symptoms, and input fields.

39 Claims, 4 Drawing Sheets

U.S. PATENT DOCUMENTS

| | | |
|---|---|---|
| 5,077,666 A | 12/1991 | Brimm et al. |
| 5,086,391 A | 2/1992 | Chambers |
| 5,109,399 A | 4/1992 | Thompson |
| 5,122,959 A | 6/1992 | Nathanson et al. |
| 5,193,855 A | 3/1993 | Shamos |
| 5,228,449 A | 7/1993 | Christ et al. |
| 5,253,164 A | 10/1993 | Holloway et al. |
| 5,255,187 A | 10/1993 | Sorensen |
| 5,291,399 A | 3/1994 | Chaco |
| 5,323,444 A | 6/1994 | Ertz et al. |
| 5,339,351 A | 8/1994 | Hoskinson et al. |
| 5,348,008 A | 9/1994 | Bornn et al. |
| 5,379,337 A | 1/1995 | Castillo et al. |
| 5,404,292 A | 4/1995 | Hendrickson |
| 5,410,471 A | 4/1995 | Alyfuku et al. |
| 5,423,061 A | 6/1995 | Fumarolo et al. |
| 5,438,996 A | 8/1995 | Kemper et al. |
| 5,441,047 A | 8/1995 | David et al. |
| 5,462,051 A | 10/1995 | Oka et al. |
| 5,471,382 A | 11/1995 | Tallman et al. |
| 5,502,726 A | 3/1996 | Fischer |
| 5,513,993 A | 5/1996 | Lindley et al. |
| 5,516,702 A | 5/1996 | Senyei et al. |
| 5,521,812 A | 5/1996 | Feder et al. |
| 5,536,084 A | 7/1996 | Curtis et al. |
| 5,544,649 A | 8/1996 | David et al. |
| 5,554,031 A | 9/1996 | Moir et al. |
| 5,590,269 A | 12/1996 | Kruse et al. |
| 5,594,638 A | 1/1997 | Iliff |
| 5,594,786 A | 1/1997 | Chaco et al. |
| 5,596,994 A | 1/1997 | Bro |
| 5,630,125 A | 5/1997 | Zellweger |
| 5,636,873 A | 6/1997 | Sonsteby |
| 5,650,995 A | 7/1997 | Kent |
| 5,660,176 A | 8/1997 | Iliff |
| 5,675,372 A | 10/1997 | Aguayo, Jr. et al. |
| 5,682,419 A | 10/1997 | Grube et al. |
| 5,684,860 A | 11/1997 | Milani et al. |
| 5,689,229 A | 11/1997 | Chaco et al. |
| 5,719,918 A | 2/1998 | Serbetciouglu et al. |
| 5,722,418 A | 3/1998 | Bro |
| 5,724,983 A | 3/1998 | Selker et al. |
| 5,734,706 A | 3/1998 | Windsor et al. |
| 5,745,532 A | 4/1998 | Campana, Jr. |
| 5,748,907 A | 5/1998 | Crane |
| 5,754,960 A | 5/1998 | Downs et al. |
| 5,759,044 A | 6/1998 | Redmond |
| 5,761,278 A | 6/1998 | Pickett et al. |
| 5,761,493 A | 6/1998 | Blakeley et al. |
| 5,787,429 A | 7/1998 | Nikolin, Jr. |
| 5,805,670 A | 9/1998 | Pons et al. |
| 5,809,493 A | 9/1998 | Ahamed et al. |
| 5,822,544 A | 10/1998 | Chaco et al. |
| 5,823,948 A | 10/1998 | Ross, Jr. et al. |
| 5,826,077 A | 10/1998 | Blakeley et al. |
| 5,832,187 A | 11/1998 | Pedersen et al. |
| 5,842,173 A | 11/1998 | Strum et al. |
| 5,844,817 A | 12/1998 | Lobley et al. |
| 5,850,611 A | 12/1998 | Krebs |
| 5,857,966 A * | 1/1999 | Clawson ............... 600/300 |
| 5,901,214 A | 5/1999 | Shaffer et al. |
| 5,902,234 A | 5/1999 | Webb |
| 5,910,987 A | 6/1999 | Ginter et al. |
| 5,912,818 A | 6/1999 | McGrady et al. |
| 5,915,019 A | 6/1999 | Ginter et al. |
| 5,926,526 A | 7/1999 | Rapaport et al. |
| 5,933,780 A | 8/1999 | Connor et al. |
| 5,961,446 A | 10/1999 | Beller et al. |
| 5,962,891 A | 10/1999 | Arai |
| 5,964,700 A | 10/1999 | Tallman et al. |
| 5,986,543 A | 11/1999 | Johnson |
| 5,989,187 A | 11/1999 | Clawson |
| 5,991,730 A | 11/1999 | Lubin et al. |
| 5,991,751 A | 11/1999 | Rivette et al. |
| 6,004,266 A | 12/1999 | Clawson |
| 6,010,451 A | 1/2000 | Clawson |
| 6,022,315 A | 2/2000 | Iliff |
| 6,035,187 A | 3/2000 | Franza |
| 6,040,770 A | 3/2000 | Britton |
| 6,052,574 A | 4/2000 | Smith, Jr. |
| 6,053,864 A | 4/2000 | Clawson |
| 6,058,179 A | 5/2000 | Shaffer et al. |
| 6,074,345 A | 6/2000 | van Oostrom et al. |
| 6,076,065 A | 6/2000 | Clawson |
| 6,078,894 A | 6/2000 | Clawson et al. |
| 6,106,459 A | 8/2000 | Clawson |
| 6,112,083 A | 8/2000 | Sweet et al. |
| 6,115,646 A | 9/2000 | Fiszman et al. |
| 6,117,073 A | 9/2000 | Jones et al. |
| 6,118,866 A | 9/2000 | Shtivelman |
| 6,127,975 A | 10/2000 | Maloney |
| 6,134,105 A | 10/2000 | Lueker |
| 6,292,542 B1 | 9/2001 | Bilder |
| 6,370,234 B1 | 4/2002 | Kroll |
| 6,535,121 B2 | 3/2003 | Matheny |
| 6,594,634 B1 | 7/2003 | Hampton et al. |
| 6,607,481 B1 | 8/2003 | Clawson |
| 6,610,012 B2 | 8/2003 | Mault |
| 6,696,956 B1 | 2/2004 | Uchida et al. |
| 6,879,819 B2 | 4/2005 | Brooks |
| 6,901,397 B1 | 5/2005 | Moldenhauer et al. |
| 6,931,112 B1 | 8/2005 | McFarland et al. |
| 6,968,375 B1 | 11/2005 | Brown |
| 7,106,835 B2 | 9/2006 | Saalsaa |
| 7,194,395 B2 | 3/2007 | Genovese |
| 7,289,944 B1 | 10/2007 | Genovese |
| 7,428,301 B1 | 9/2008 | Clawson |
| 7,436,937 B2 | 10/2008 | Clawson |
| 7,645,234 B2 | 1/2010 | Clawson |
| 7,703,020 B2 | 4/2010 | Bhattaru |
| 2002/0004729 A1 | 1/2002 | Zak et al. |
| 2002/0106059 A1 | 8/2002 | Kroll et al. |
| 2003/0028536 A1 | 2/2003 | Singh et al. |
| 2003/0050538 A1 | 3/2003 | Naghavi et al. |
| 2003/0187615 A1 | 10/2003 | Epler et al. |
| 2003/0195394 A1 | 10/2003 | Saalsaa |
| 2003/0212575 A1 | 11/2003 | Saalsaa et al. |
| 2006/0059423 A1 | 3/2006 | Lehmann et al. |
| 2006/0122520 A1 | 6/2006 | Banet et al. |
| 2006/0167346 A1 | 7/2006 | Sarel |
| 2006/0173500 A1 | 8/2006 | Walker et al. |
| 2006/0178908 A1 | 8/2006 | Rappaport |
| 2006/0212315 A1 | 9/2006 | Wiggins |
| 2007/0055559 A1 | 3/2007 | Clawson |
| 2007/0112275 A1 | 5/2007 | Cooke et al. |
| 2007/0116189 A1 | 5/2007 | Clawson |
| 2007/0201664 A1 | 8/2007 | Salafia et al. |
| 2008/0208801 A1* | 8/2008 | Friedlander et al. .............. 707/3 |
| 2009/0168975 A1 | 7/2009 | Clawson |
| 2009/0191529 A1 | 7/2009 | Mozingo et al. |
| 2010/0004710 A1 | 1/2010 | Kellum |
| 2010/0121156 A1 | 5/2010 | Yoo |
| 2010/0152800 A1 | 6/2010 | Walker et al. |
| 2010/0198755 A1 | 8/2010 | Soll et al. |
| 2010/0257250 A1 | 10/2010 | Salafia et al. |
| 2011/0064204 A1 | 3/2011 | Clawson |

FOREIGN PATENT DOCUMENTS

| | | |
|---|---|---|
| JP | 2003-187003 A | 7/2003 |
| JP | 2003256963 A | 9/2003 |
| JP | 2010033201 A | 12/2010 |
| KR | 10-2005-0085778 A | 8/2005 |
| KR | 10-2006-0084866 A | 7/2006 |
| KR | 20070043337 A | 4/2007 |
| KR | 10-2008-0004125 A | 1/2008 |
| WO | WO2006/015229 A2 | 2/2006 |
| WO | WO2008/156876 A1 | 12/2008 |

OTHER PUBLICATIONS

International Search Report and Written Opinion mailed Jan. 19, 2011 in PCT Application No. PCT/US2010/043311, filed Jul. 27, 2010.

International Search Report and Written Opinion PCT/US2010/050402, filed on Sep. 27, 2010, and mailed from ISA on Apr. 27, 2011, 9 pgs.

International Preliminary Report of Patentability for PCT/US2009/048577 filed on Jun. 25, 2009 mailed Oct. 27, 2011, 7 pgs.
International Search Report and Written Opinion for PCT/US2011/042543 filed on Jun. 30, 2011, and mailed from ISA on Feb. 9, 2012, 11 pgs.
International Search Report and Written Opinion for PCT/US2011/042582 filed on Jun. 30, 2011, and mailed from ISA on Feb. 9, 2012, 8 pgs.
International Preliminary Report of Patentability for PCT/US2010/043308 filed on Jul. 27, 2010 mailed Mar. 22, 2012, 6 pgs.
International Preliminary Report of Patentability for PCT/US2010/043311 filed on Jul. 27, 2010 mailed Mar. 29, 2012, 6 pgs.
Office Action Summary from USPTO for U.S. Appl. No. 12/558,045 mailed Mar. 22, 2012, 9 pgs.
Office Action for U.S. Appl. No. 12/268,963, filed Nov. 11, 2008, mailed from USPTO on Jul. 29, 2011, 18 pgs.
Office Action for U.S. Appl. No. 12/396,201, filed Mar. 2, 2009 and mailed from USPTO on Mar. 8, 2011, 23 pgs.
Radosevich, Lynda, "Network holds sway on life, death," Computerworld, v27 n21, May 24, 1993, 2 pgs.
Harris, Roger, "Updated 911 Phone System Top Concern of Residents," Business First-Louisville, v9 n19 s1, Dec. 1992, 3 pgs.
"Geac Completes Software Install," Wireless Week, Nov. 18, 1996, 3 pgs.
"Dictaphone introduces Windows-based Computer-Aided Dispatch (CAD) system," Business Wire, Apr. 23, 1996, 2 pgs. (in commercial use in 1995).
Holroyd, Brian, et al., "Medical Control; Quality Assurance in Prehospital Care," JAMA, the Journal of American Medical Association, v256, n8, Aug. 1986, p. 1027-1031.
CBS web page News Story entitled "911 Operator: 'It's got to be Hell'", Mar. 31, 2006 (excerpts from 911 operators' actions during the attacks on Sep. 11, 2001), 3 pgs.
Best, Wendy, "999 United Emergency services share life-saving Role to boost response," Western Daily Press, WDP Severnside ed., May 27, 1999, 2 pgs.
Poellmitz, William C., "Wireless technology keeps public safety a step ahead," Nation's Cities Weekly, v21 n17, Apr. 27, 1998, 3 pgs.
Crowley, Mark, "Learning from CAD System Implementation," Communications, v29 n8, Aug. 1992, 5 pgs.
Anonymous, "Suburban Chicago towns centralize 911 services," Communications News, v31 n10, Oct. 1994, 2 pgs.
Office Action Summary from USPTO for U.S. Appl. No. 10/255,901 mailed Dec. 31, 2003, 8 pgs.
Office Action Summary from USPTO for U.S. Appl. No. 10/255,901 mailed Oct. 13, 2004, 8 pgs.
Office Action Summary from USPTO for U.S. Appl. No. 10/255,901 mailed Jun. 29, 2005, 7 pgs.
Advisory Action Before the Filing of an Appeal Brief from USPTO for U.S. Appl. No. 10/255,901 mailed Feb. 14, 2006, 3 pgs.
Office Action Summary from USPTO for U.S. Appl. No. 10/255,901 mailed Jun. 7, 2006, 8 pgs.
Office Action Summary from USPTO for U.S. Appl. No. 10/255,901 mailed Feb. 27, 2007, 8 pgs.
Office Action Summary from USPTO for U.S. Appl. No. 10/255,901 mailed Sep. 6, 2007, 9 pgs.
Office Action Summary from USPTO for U.S. Appl. No. 10/255,905 mailed May 19, 2004, 7 pgs.
Office Action Summary from USPTO for U.S. Appl. No. 10/255,905 mailed May 26, 2005, 5 pgs.
Office Action Summary from USPTO for U.S. Appl. No. 10/255,905 mailed Feb. 9, 2006, 8 pgs.
Advisory Action Before the Filing of an Appeal Brief from USPTO for U.S. Appl. No. 10/255,905 mailed Aug. 11, 2006, 3 pgs.
Office Action Summary from USPTO for U.S. Appl. No. 10/255,905 mailed Jan. 30, 2007, 7 pgs.
Notice of Non-Compliant Amendment (37 CFR 1.121) from USPTO for U.S. Appl. No. 10/255,905 mailed Jul. 9, 2007, 4 pgs.
Office Action Summary from USPTO for U.S. Appl. No. 10/255,905 mailed Oct. 5, 2007, 7 pgs.
Office Action Summary from USPTO for U.S. Appl. No. 09/685,697 mailed Jul. 18, 2003, 8 pgs.
Office Action Summary from USPTO for U.S. Appl. No. 09/685,697 mailed Feb. 3, 2004, 5 pgs.
Office Action Summary from USPTO for U.S. Appl. No. 09/685,697 mailed Jan. 4, 2005, 5 pgs.
Office Action Summary from USPTO for U.S. Appl. No. 09/685,697 mailed Oct. 4, 2005, 7 pgs.
Advisory Action Before the Filing of an Appeal Brief from USPTO for U.S. Appl. No. 09/685,697 mailed Mar. 13, 2006, 4 pgs.
Office Action Summary from USPTO for U.S. Appl. No. 09/685,697 mailed Jun. 26, 2006, 8 pgs.
Office Action Summary from USPTO for U.S. Appl. No. 09/685,697 mailed Apr. 10, 2007, 9 pgs.
Office Action Summary from USPTO for U.S. Appl. No. 09/685,697 mailed Oct. 9, 2007, 11 pgs.
Office Action Summary from USPTO for U.S. Appl. No. 10/140,635 mailed Oct. 3, 2003, 9 pgs.
Office Action Summary from USPTO for U.S. Appl. No. 10/140,635 mailed Jul. 16, 2004, 11 pgs.
Office Action Summary from USPTO for U.S. Appl. No. 10/140,635 mailed Apr. 19, 2005, 11 pgs.
Office Action Summary from USPTO for U.S. Appl. No. 10/140,635 mailed Jan. 17, 2006, 13 pgs.
Office Action Summary from USPTO for U.S. Appl. No. 10/140,635 mailed Sep. 20, 2006, 15 pgs.
Office Action Summary from USPTO for U.S. Appl. No. 10/140,635 mailed Jun. 21, 2007, 15 pgs.
International Search Report for PCT/US2008/054987 filed on Feb. 26, 2008, and mailed on Oct. 8, 2008, 2 pgs.
Written Opinion of the International Searching Authority for PCT/US2008/054987 filed on Feb. 26, 2008, and mailed on Oct. 8, 2008, 9 pgs.
Notification of Transmittal of the International Search Report (2 pgs.), International Search Report, (2 pgs.), and Written Opinion (8 pgs.) mailed from International Searching Authority on Jun. 10, 2009.
International Search Report and Written Opinion for PCT/US09/48577, International filing date Jun. 25, 2009, mailed from ISA Aug. 7, 2009, 9 pgs.
Office Action Summary from USPTO for U.S. Appl. No. 12/422,561 mailed Jul. 3, 2012, 23 pgs.
International Search Report and Written Opinion for PCT/US2012/021867 filed Jan. 19, 2012, and mailed Aug. 30, 2012, 9 pgs.

* cited by examiner

PANDEMIC DIAGNOSTIC AND INTERVENTION TOOL FOR EMERGENCY DISPATCH

COPYRIGHT NOTICE

©2009 Priority Dispatch Corp. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71(d).

TECHNICAL FIELD

This invention relates to computer systems and methods for providing medical protocol interrogation, instruction, and emergency dispatch. More specifically, the invention is directed to computer-implemented tools to assist a dispatcher during an interrogation and instruction of an emergency caller.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION

Figure 1:
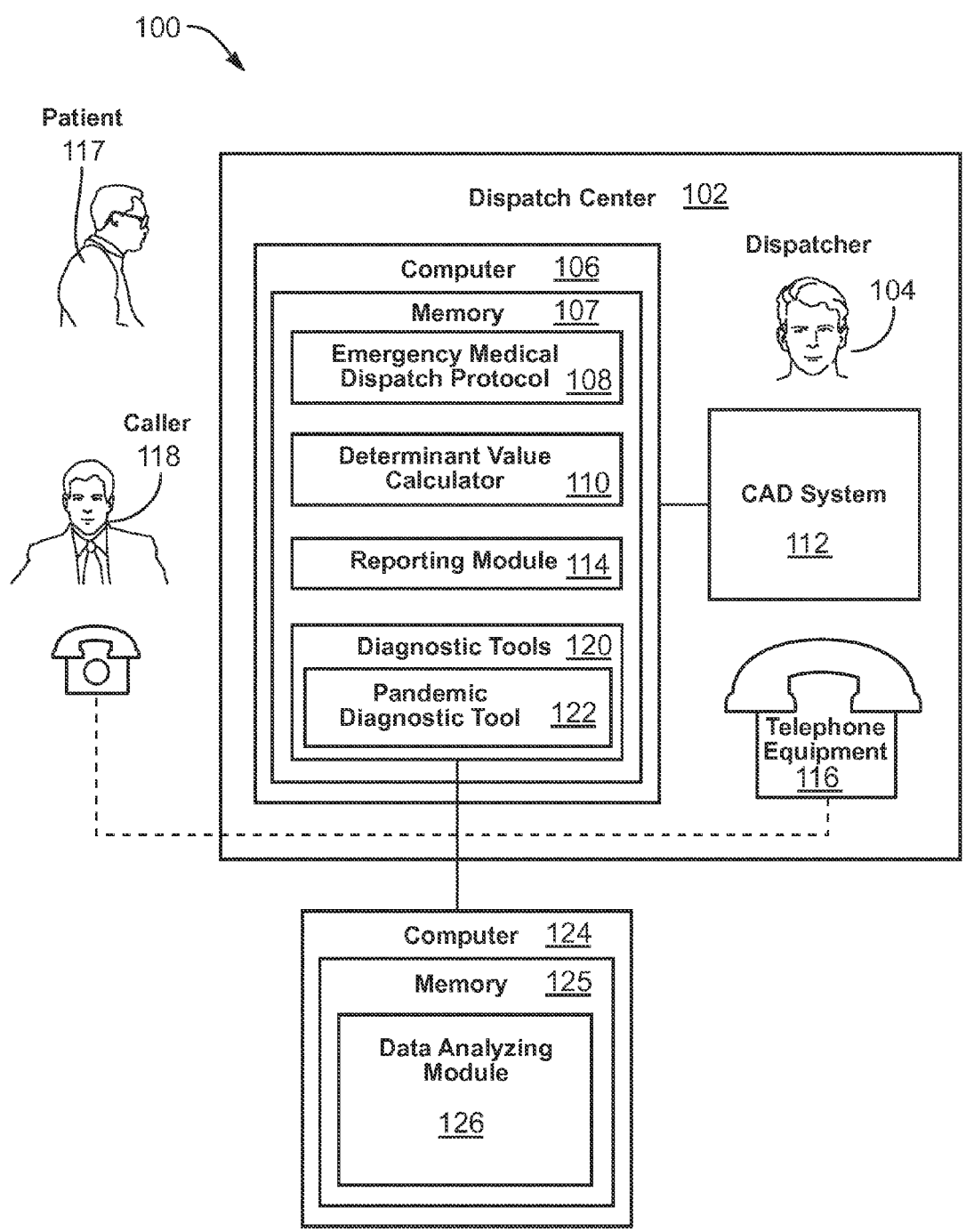
FIG. 1 is a block diagram of an emergency medical dispatch system, according to one embodiment.

A pandemic outbreak (or simply a pandemic) involves an infectious disease that is prevalent over a widespread geographic area and that affects a large proportion of the population. An epidemic may be considered a pandemic on a smaller scale. A pandemic is significant and concerning because of the potential that all individuals of the public may be at risk of suffering serious illness or death. A pandemic can cause fear and apprehension, can close schools, places of business, and other public places. A pandemic can also potentially disrupt economic activity and development, thereby introducing other far-reaching effects.

A pandemic is also concerning because it can place sudden and intense demands on healthcare systems. The rampant nature by which a pandemic can spread requires a large proportion of available healthcare resources and providers to treat the victims of the illness. Especially concerning is that the infectious nature of a pandemic illness puts at risk the healthcare providers who are trained to treat the illness and stop it from spreading. In other words, a pandemic can be dangerous for the public at large because of the demands on and risks posed to the public's defense mechanism against the illness, namely the healthcare systems and healthcare providers (collectively "healthcare providers").

While public health officials agree that a pandemic is a concerning and significant situation, not all agree on the criteria that characterize a pandemic. The size of a geographic region and the proportion of a population of that region that must be affected to constitute a pandemic are criteria that are inherently ambiguous, subjective, and relative, and consequently are constantly subject to debate. Views diverge as to the appropriate standard for initially categorizing an outbreak of an illness as an epidemic, and the appropriate standard for categorizing when an outbreak then becomes a pandemic. Various local, national, and international health officials and organizations have established standards of criteria to define a pandemic (and an epidemic), and understandably not all are alike. Despite the diverging standards, a person of ordinary skill will appreciate that an infectious disease posing a threat to spread among the public, whether of epidemic or pandemic proportions, and whether unofficially or officially categorized as such, creates a situation with issues and concerns analogous to those of a clearly severe pandemic. Accordingly, as used herein, the term pandemic can encompass all situations relating to an infectious disease spreading, or posing a threat to spread, among a population. A pandemic illness is an infectious disease that is spreading or posing a threat to spread among a population.

The infectious nature of a pandemic, the threat to the public at large, and the risks posed to healthcare providers may suggest that an emergency response tailored to the particular pandemic illness would be beneficial. For example, there may be reason for heightened precautions and procedures, reason to monitor the location of the illness and track its progress, and reason to isolate or even quarantine cases of the illness. Unfortunately, existing methods and systems offer little to facilitate providing an appropriate emergency response to an emergency situation involving a pandemic illness. Existing methods and systems for gathering information to monitor and track a pandemic outbreak gather the desired information too long after the onset of a case and without the consistency or uniformity to make the information readily useable.

Often a case remains unreported until treatment by a trained healthcare provider. Sometimes the pandemic illness is not easily identifiable by someone without medical training. Thus, the illness simply may not be affirmatively identified prior to diagnosis by a trained healthcare provider. Unfortunately, from a reporting standpoint, a healthcare provider is typically focused primarily on treating the illness rather than reporting or tracking the outbreak. Healthcare providers may not report a case until after treatment, after test results, or potentially even until after the patient's death. Earlier reporting is better, but systems and methods may not be available and non-healthcare providers may not know or understand the importance or the process of reporting the case.

Even when a case is immediately reported, the manner by which the reporting source reports the case may be inconsistent and sporadic. Thus, the information or data that results from collecting the reported information tends to be disorderly, unmanageable, and nearly unusable. (In description that follows, the terms "information" and "data" may be used interchangeably, and are not to be construed as limiting in anyway. However, as clarification, the term "data" as used herein may primarily refer to information after it is collected, which may be combined with data for other cases and used to monitor and track a pandemic. The terms "gather" and "collect" may also be used interchangeably herein, and are not to be construed as limiting in anyway. However, the term "collect" may primarily contemplate compiling and/or formatting symptom information into data.)

Reporting sources (e.g., healthcare providers, health officials, agencies, individuals, etc.) may gather and report the information regarding a case of an illness in a different way. As an example, a symptom as basic as a "fever" can be communicated in numerous ways, including but not limited to "high temperature," "severe fever," "temperature of 103.5 degrees," "fever of 103°," "high fever," "high grade fever," etc. Depending on the reporting method, skill, experience, and/or sophistication of the reporting source, and numerous other factors, each of these ways of communicating the same symptom information may be accurate, correct, and appropriate. As a result, extensive reformatting and processing of the information is necessary to make the resulting data measurable, such that the various reported cases can be compared and trends can be identified and monitored from the collected data.

Also problematic is that not every reporting source will address the same symptoms. For example, one reporting source may report that the patient of a first case has a fever and has difficulty breathing. Another reporting source may report that the patient of a second case has a fever, but perhaps never considered whether or not the patient may be having difficulty breathing. Without a check or other measure of confidence that the breathing of the patient was considered, an omission of the symptom "having difficulty breathing" simply cannot be assumed to mean that the patient is breathing normally. The set of symptoms considered from case to case may not be substantially uniform, thereby limiting the measurability and usability of the information to track and monitor trends of the illness.

Consider as an illustrative example the information gathering process of the World Health Organization (WHO), which gathers official reports and rumors of suspected outbreaks from a wide range of sources. The WHO obtains official reports from formal reporting sources, including ministries of health, national institutes of public health, WHO Regional and Country offices, laboratories, and academic institutes. Each of these formal reporting sources is typically at least one degree removed from actual contact with victims of the illness, because these reports are typically compiled from information initially gathered and reported by a different reporting source, such as a third-party healthcare provider. Each of these reporting sources (both the formal reporting sources and the initial reporting sources) may have its own unique reporting method and format. The formal reporting sources may have protocols in place with the WHO to improve uniformity of reported information, but the initial reporting sources likely do not. There is little certainty that each of the initial reporting sources is reporting to the formal reporting source using the same format and considering all the same symptoms as all of the other initial reporting sources.

The Center for Disease Control and Prevention (CDC) may be an example of a formal reporting source, which gathers official reports from similar formal sources at a national level and reports to the WHO. The CDC faces similar reporting and collecting challenges prior to reporting to the WHO. As a result, a tremendous amount of processing, massaging, and/or interpreting of the data is necessary at each level of reporting to make use of the reported information. The processing, massaging, and/or interpreting of the data is costly, time consuming, and prone to introduce errors and inconsistency into the data.

The WHO and the CDC also attempt to gather information from a variety of informal sources. In particular, with the advent of modern communication technologies, many initial outbreak reports now originate in the electronic media and electronic discussion groups. As can be appreciated, any initial outbreak report that comes from an informal source may be in a unique format and contain information that is from a unique set of information. Consequently, reports from informal sources may require verification. Verification generally includes a medical provider affirmatively diagnosing a case and reporting the information of the outbreak. The verification report by the healthcare provider, however, may not be any more uniform or consistent in format or information set than a report provided by the informal source, for the reasons already explained.

At least three problems are apparent from existing methods and systems. First, reporting by healthcare providers may be untimely and inconsistent. Second, reporting by non-healthcare providers may lack accuracy and confidence. Third, the information obtained from healthcare providers and non-healthcare providers may not be useful or measurable due to lack of uniformity and consistency of the information. The present disclosure recognizes that these and other shortcomings of existing methods and systems may be overcome by gathering the desired information earlier, at a point substantially contemporaneous with the appearance of the first signs or symptoms of the case of the illness, and by facilitating gathering pandemic symptom and patient information in a consistent, uniform manner.

Emergency dispatchers are often an early (if not the earliest) interface with healthcare providers when an emergency strikes. In particular, emergency dispatchers process emergency calls relating to a wide variety of emergency situations, including emergencies involving symptoms and/or cases of the pandemic illness. Dispatchers often play a role in dispatching emergency responders including healthcare providers to the scene of the emergency. The dispatchers in effect send the medical care, coordinating the first interaction between a patient and a healthcare provider. As an early interface, emergency dispatchers are well positioned to play a role in gathering information to track, monitor, and isolate the pandemic disease.

Often emergency dispatchers are inexperienced and unskilled, largely due to a high turnover rate among emergency dispatchers. An automated emergency dispatch system, potentially implemented on a computer, can aid a dispatcher in prioritizing the varying types of emergency calls received and in processing the calls to generate an appropriate emergency dispatch response. Regardless of the experience or skill level of the dispatcher, the automated emergency dispatch systems can enable a consistent and predictable emergency dispatch response, despite the diverse aspects of emergency situations, including inter alia signs, symptoms, conditions, and circumstances, that may be reported from one call to the next.

Although an automated emergency dispatch system can enable receiving and processing of widely divergent aspects of emergency situations, these systems may not be well suited for exploring any particular type of situation in depth. An emergency situation relating to a pandemic illness, or involving symptoms of such illness, may require probing and in-depth exploration of the symptoms at the time that the situation is reported. The further exploration may require the dispatcher to probe more deeply to gather more descriptive details of the symptoms the patient may be manifesting. Moreover, emergency situations involving a pandemic illness may be considered to occur within the context of a larger public emergency. An emergency situation involving the pandemic illness should be handled on an individual basis, but also with the larger community in mind and with an objective of tracking and even containing the illness. Precautions must be taken to ensure that it is properly tracked and handled. As such, the emergency situations involving a pandemic illness may benefit from more detailed instructions. Additional interrogation, instructions, and/or alternative emergency dispatch procedures or protocols may facilitate tracking and/or containing the pandemic illness.

Existing automated emergency dispatch systems are not equipped to assist or enable a dispatcher to explore an emergency call involving a pandemic illness. Automated emergency dispatch systems are better configured for handling a broad spectrum of emergencies, rather than to explore specific types of situations in greater depth to gather symptom information and provide further instruction. In particular, exploring a situation to gather more detailed information may be difficult and cumbersome within the protocol of the emergency dispatch system.

A dispatcher with little or no medical training or experience likely cannot compensate for the shortcomings of an automated emergency dispatch system. Inexperienced and/or unskilled dispatchers are generally unable to properly explore situations and/or aspects or diagnose medical conditions, let alone instruct a caller to do so. Even highly skilled and experienced dispatchers may have little skill or experience with handling pandemic situations, simply because pandemic emergencies are relatively rare. Accordingly, the present disclosure provides a diagnostic tool to supplement an automated emergency dispatch system and enable consistent and uniform gathering of information.

The embodiments of the disclosure will be best understood by reference to the drawings, wherein like parts are designated by like numerals throughout. It will be readily understood that the components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

In some cases, well-known features, structures or operations are not shown or described in detail. Furthermore, the described features, structures, or operations may be combined in any suitable manner in one or more embodiments. It will also be readily understood that the components of the embodiments as generally described and illustrated in the figures herein could be arranged and designed in a wide variety of different configurations.

Several aspects of the embodiments described will be illustrated as software modules or components. As used herein, a software module or component may include any type of computer instruction or computer executable code located within a memory device and/or computer-readable storage medium. A software module may, for instance, comprise one or more physical or logical blocks of computer instructions, which may be organized as a routine, program, object, component, data structure, etc. that performs one or more tasks or implements particular abstract data types.

In certain embodiments, a particular software module may comprise disparate instructions stored in different locations of a memory storage device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network.

In a distributed computing environment, software modules may be located in local and/or remote memory storage devices. In addition, data being tied or rendered together in a database record may be resident in the same memory device, or across several memory devices, and may be linked together in fields of a record in a database across a network.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

An emergency dispatch system as disclosed herein may be computer-implemented in whole or in part on a digital computer. The digital computer includes a processor performing the required computations. The computer further includes a memory in electronic communication with the processor for storing a computer operating system. The computer operating systems may include MS-DOS, Windows, Linux, Unix, AIX, CLIX, QNX, OS/2, and Apple. Alternatively, it is expected that future embodiments will be adapted to execute on other future operating systems. The memory also stores application programs including a Computer Aided Dispatch (CAD) program, an automated emergency dispatch protocol, a user interface program, and data storage. The computer may further include an output device, such as a display unit, for viewing the displayed instructions and inquiries and a user input device for inputting response data.

FIG. 1 is an emergency medical dispatch system 100, according to one embodiment. At a dispatch center 102, a dispatcher 104 operates a computer 106. The computer may include a memory 107 to store protocols, modules, tools, data, etc. The computer 106 may be configured to execute an emergency medical dispatch protocol 108 to enable the dispatcher to rapidly and consistently address a medical emergency of a patient 117 as reported by a caller 118. The emergency medical dispatch protocol 108 provides a logic tree with questions, possible responses from a caller 118, and instructions to the caller 118. The responses may route to subsequent questions and/or instructions to the caller. The responses are processed according to predetermined logic of the logic tree to both provide to the dispatcher 104 the correct emergency medical dispatch response (e.g., by trained emergency responders) and the appropriate doctor-approved post-dispatch instructions for relay to the caller 118 before professional help arrives at the scene. The emergency medical dispatch system 100 may also aid the dispatcher in determining an appropriate priority of the emergency call, including but not limited to a priority of the emergency call relative to other emergency calls and the level of emergency response provided for the emergency.

Although an emergency medical dispatch system 100 and emergency medical dispatch protocol 108 are disclosed and described herein, a person of ordinary skill can appreciate that other emergency dispatch systems and protocols are contemplated, including but not limited to emergency fire dispatch systems and protocols and emergency police dispatch systems and protocols. Exemplary embodiments of emergency dispatch systems and protocols are disclosed in U.S. Pat. Nos. 5,857,966, 5,989,187, 6,004,266, 6,010,451, 6,053,864, 6,076,065, 6,078,894, 6,106,459, 6,607,481, 7,106,835, and 7,428,301, which are incorporated herein by reference.

The computer 106 may operate a determinant value calculator 110 to calculate a determinant value from the responses of the caller 118 to protocol questions. The computer 106 presents the determinant value to generate an appropriate emergency dispatch response and/or establish the priority of the emergency call. The response may include dispatching professional emergency responders to the scene of the emergency. Because the questions asked and the recommendations that are made deal directly with life and death decisions, the protocols used shall have passed through a rigorous medical review by a panel of doctors and EMS public safety experts who specialize in emergency medicine. The determinant value calculator 110 may be stored on the memory 107 of the computer.

Many calls for medical services are not true medical emergencies, so it is important to prioritize the calls in several ways. First, calls that are true emergencies should be dispatched first. Second, if an agency has units with different capabilities, more advanced units can be sent to handle more severe medical problems. And finally, if lights-and-siren are not needed from a medical standpoint, they should not be used, thereby increasing the safety of all those on the road and in the emergency vehicles. While many medical calls are not true emergencies, all situations can benefit from medical evaluation and instruction. Prior to the arrival of professional help on-scene, the emergency medical dispatch protocol 108 provides the dispatcher 104 with instructions for the caller 118 that are appropriate to the type of call, whether for a patient 117 with minor lacerations or a patient 117 who is not breathing.

The determinant value provides a categorization code of the type and level of the incident. The code may be provided to a Computer Aided Dispatch (CAD) system 112, which is a tool used by a dispatcher 104 to track and allocate emergency response resources, for processing emergency calls. The CAD may manage dispatcher tools for processing emergency calls, including but not limited to the emergency dispatch protocol 108, communication resources (e.g., radio system, alpha pager), mapping tools (e.g., global positioning system (GPS) technology), and vehicle location systems (e.g., automatic vehicle location (AVL)). The CAD system 112 may operate in whole or in part on a separate computer in communication with computer 106. In another embodiment, the CAD system 112 operates on computer 106. The primary information used by the CAD system 112 is location information of both the incident and units, unit availability and the type of incident. The CAD system 112 may use third party solutions, such as E-911, vehicle location transponders and mobile data terminals (MDT's) for automating the location and availability tasks. The CAD system may also use an emergency dispatch protocol 108 to facilitate structured call taking for incident interrogation, as previously described.

The computer 106 may also include a reporting module 114 to statistically measure the performance of individual staff and overall performance of the dispatch center 102. These statistics include compliance rates, call processing statistics, and peer measurements. The reporting module 114 may be stored on the memory 107 of the computer 106.

The computer 106 may further comprise an input device such as a keyboard, mouse, or other input device and also an output device such as a display monitor. The input device receives input from a user (generally a dispatcher) and provides it to the emergency medical dispatch system 100. The input may be provided to the computer 106, the emergency dispatch protocol 108, the diagnostic tools 120, and/or the CAD system 112. The output device receives output from the emergency medical dispatch system 100 and displays or otherwise presents the output to the user. In another embodiment, the input device and output device are provided by the CAD system 112. In still another embodiment, the CAD system 112 runs on the computer 106.

The dispatch center 102 includes telephony equipment 116 to answer emergency calls. A call into the dispatch center 102 from a caller 118 initiates creation of a medical call incident. The dispatcher 104 identifies the call as requiring an emergency medical dispatch, and the emergency medical dispatch protocol 108 is accessed. The protocol 108 may provide instructions that are expertly drafted to assist a novice caller 118 in diagnosing a condition of a patient 117. The protocol 108 may also provide expertly drafted first aid instructions to assist a patient 117 prior to the arrival of trained emergency responders. The instructions may be vocally relayed by the dispatcher 104 to the caller 118 over the telephony equipment 116.

Some protocol questions may be readily answerable by the caller 118, whereas others are more difficult to answer. Certain diagnostic inquiries may be difficult for the untrained caller to determine or may be difficult to answer under the stress of an emergency situation. Accordingly, in addition to instructions, the emergency medical dispatch system 100 may provide one or more computer-implemented diagnostic tools 120. The diagnostic tools 120 may greatly improve information collection and intervention for emergency medical response situations and aid in saving lives.

A diagnostic tool 120 may aid the dispatcher and/or the caller (via instructions from the dispatcher) in diagnosing a condition of a patient 104. A diagnostic tool 120 may also be an interventional tool, providing instructions that direct a caller to intervene, or take action, to treat a patient 104, or otherwise change the circumstances or conditions of an emergency situation. For sake of clarity, diagnostic tools and interventional tools are both referred to herein generally as diagnostic tools. Accordingly, a diagnostic tool 120, as referred to herein, may provide diagnostic instructions, interventional instructions, or both diagnostic and interventional instructions. Whether a diagnostic tool 120 provides merely diagnostic instructions, merely interventional instructions, or both diagnostic and interventional instructions, the diagnostic tool can provide consistent and reliable instruction, information gathering, and/or timing for a particular emergency situation.

The diagnostic tools 120 are computer implemented software modules that enable a dispatcher 104 to provide consistent, expert advice to assist a caller with regards to a particular aspect of an emergency situation, such as determining a vital sign. One benefit of the diagnostic tools 120 is the computer aided timing of techniques to determine the vital signs. In highly stressful conditions, the diagnostic tools 120 provide a necessary resource to reading critical signs. The diagnostic tools 120 may be stored in the memory 107 of the computer 106 and initiated and executed as required. The diagnostic tools 120 may be embodied as computer executable software applications and associated data.

The emergency medical dispatch protocol 108 also may call on a diagnostic tool 120, for example to assist with an interrogatory, and may route to the appropriate diagnostic tool 120 when needed. When directed according to the emergency dispatch protocol 108, the emergency medical dispatch system 100 may automatically, i.e., without dispatcher intervention, initiate the appropriate diagnostic tool 120 on the dispatch center computer 106. This may occur when the emergency medical dispatch protocol 108 arrives at a diagnosis step in the logic tree. The emergency medical dispatch system 100 may also allow the dispatcher 104 the option to manually call upon a diagnostic tool 120 as desired. Icons and/or buttons may be displayed in a tool bar, or other convenient location on a user interface to allow the dispatcher 104 to initiate a corresponding diagnostic tool 120.

The diagnostic tool 120 discussed herein comprises a pandemic diagnostic tool 122. The pandemic diagnostic tool 122 may be configured as a surveillance tool to collect information to identify patterns, trends, and geographical clusters of symptoms of a particular pandemic illness. The pandemic diagnostic tool 122 is configured to facilitate consistent, uniform collection of information, such that the information is gathered in substantially the same manner and seeking substantially the same set of information for all cases, regardless of the skill or experience of the dispatcher. The gathered symptom information is uniform and quantifiable and can be appropriately measured or compared against other data gathered in a similar manner. The pandemic diagnostic tool 122 may also be configured to advise emergency responders that a patient might be infected with the pandemic illness. Advanced warning that the patient might be infected enables the emergency responders to take available precautions to guard against contracting the illness and/or spreading the illness. The pandemic diagnostic tool 122 may further be configured to calculate the likelihood (or probability) that a patient is infected with the pandemic illness based on the gathered symptom information.

Without the pandemic diagnostic tool 122, dispatchers gather symptom information using varied and unsystematic approaches. There may be nearly as many ways to gather pandemic symptom information as there are emergency response agencies. For example, assuming two calls, a first dispatcher may ask three questions, whereas the second dispatcher may ask eight questions. When attempting to use the data gathered from the first and second calls, the data is nearly useless because the manner of gathering the information and the information sought varied. Thus, the data sets cannot be appropriately compared or measured against each other. By contrast, the pandemic diagnostic tool 122 aids to ensure that, no matter who gathers the symptom information, the gathering is consistently done the same way, and consistently seeks information regarding the same set of signs, symptoms, and/or criteria. Moreover, the pandemic diagnostic tool 122 can be used during a pandemic outbreak to screen every patient for symptoms of the pandemic illness.

The symptom information gathered by the pandemic diagnostic tool 122 can be used by local public health authorities to attempt to determine if pandemic outbreak may be occurring in a particular region. The symptom information gathered by the pandemic diagnostic tool 122 can be stored for tracking purposes and also communicated to emergency response agencies to alert the emergency responders of the potential for contact with the particular pandemic illness, so that they can take any potential precautionary measures.

The pandemic diagnostic tool 122 may be launched from within, or at least in conjunction with, the progression of the emergency medical dispatch protocol 108 to enhance and supplement emergency call processing facilitated by the emergency medical dispatch protocol. The pandemic diagnostic tool 122 may be launched automatically by the emergency medical dispatch protocol 108, or launched manually by a dispatcher.

The pandemic diagnostic tool 122 may be useful under a variety of circumstances, such as when a public health authority has officially declared a pandemic outbreak/emergency and information needs to be gathered to identify trends and track the geographic location and patterns of outbreaks. Moreover, during a declared pandemic, EMS, hospital, and community health care resources may be scarce due to high demand and the pandemic diagnostic tool 122 can enable management of suspected pandemic patients in a manner that utilizes these resources effectively and efficiently.

The pandemic diagnostic tool 122 is discussed below in reference to figures of graphical user interfaces that exemplify certain embodiments. One of skill in the art will appreciate that such interfaces may be implemented and designed in various ways and still be within the scope of the invention.

The emergency medical dispatch system 100 may further comprise a data analyzing module 126. The data analyzing module 126 may be stored on a memory 125 of a separate computer 124. The data analyzing module 126 processes the data collected by the pandemic diagnostic tool 122 to identify trends and track the geographic location and patterns of outbreaks. The collected data may be transmitted to the data analyzing module by the dispatch center computer system 106. In another embodiment, the data analyzing module 126 may be stored on the memory 107 of the computer 106. In still another embodiment, the data analyzing module 126 may be included as part of the CAD system 112. In still another embodiment, the data analyzing module 126 is operated by a third party, apart from the emergency medical dispatch system 100. The third party may receive collected data from a plurality of sources and the data analyzing module 126 may process data from a plurality of sources.

Figure 2:
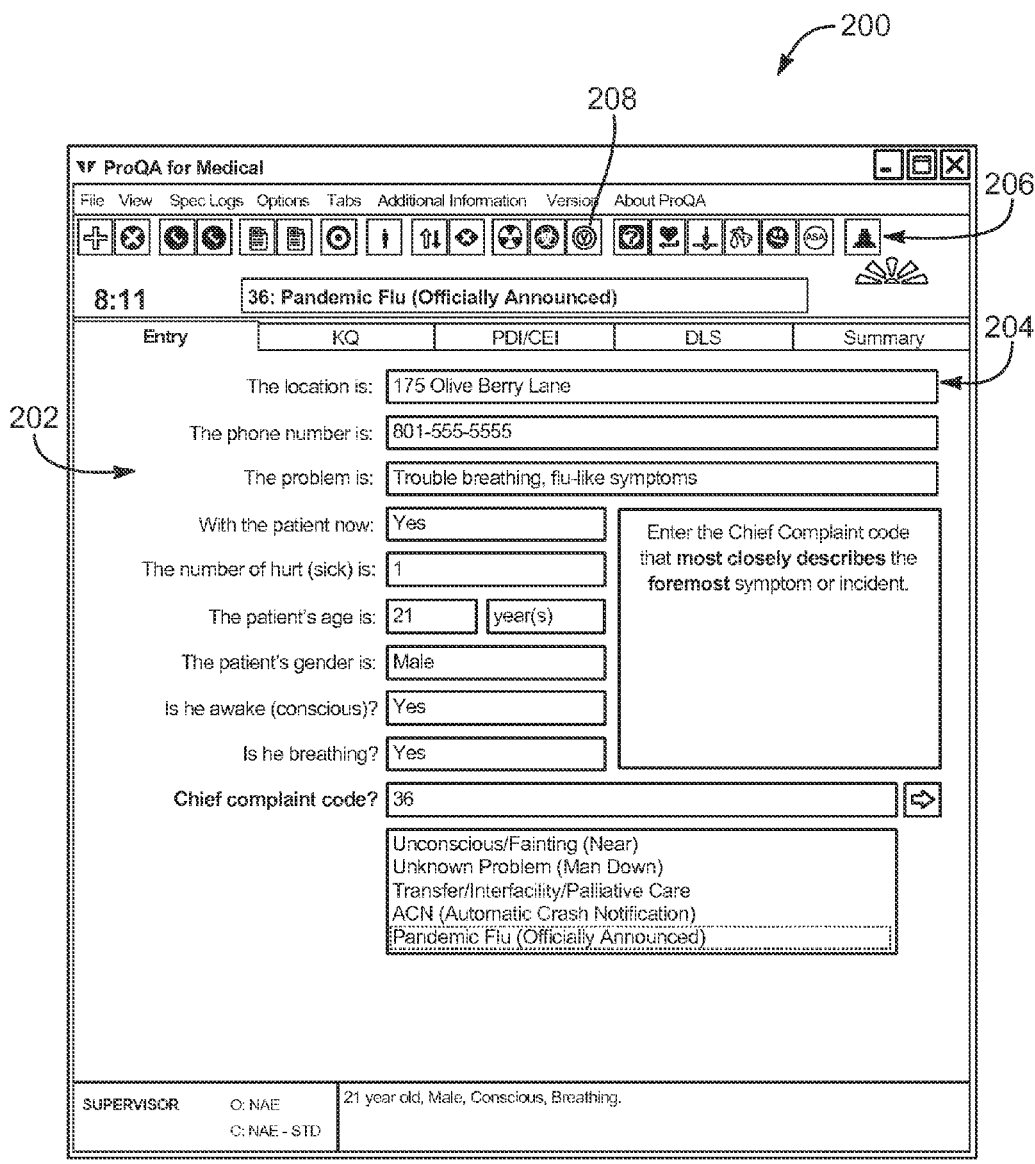
FIG. 2 illustrates a user interface of an emergency medical dispatch protocol, according to one embodiment.

FIG. 2 illustrates an embodiment of a user interface 200 of an emergency medical dispatch protocol, according to one embodiment. The emergency medical dispatch protocol user interface 200 allows a dispatcher to interface with the emergency medical dispatch protocol. The emergency medical dispatch protocol may present interrogatories 202 via the emergency medical dispatch protocol user interface 200. The interrogatories 202 are provided for the dispatcher to direct to the caller to gather information regarding the medical emergency of the patient. The dispatcher and/or the emergency medical dispatch system may gather the information in the form of caller responses to the interrogatories 202. The dispatcher may input the responses of the caller to the interrogatories into response fields 204 provided by the user interface 200. The response fields 204 may include, for example, familiar user interface components, including but not limited to text fields, text boxes, menus, drop down menus, drop-down selection boxes, lists, buttons, check boxes, and radio buttons. The response fields 204 may correspond to information indicative of one or more responses of the caller to the interrogatories 202.

The caller responses are relayed from the caller to the dispatcher. Information from the caller responses may be input into the system by the dispatcher and may be used by the emergency medical dispatch protocol to determine subsequent interrogatories 202 and instructions to present to the dispatcher. The caller response information may indicate the caller's observations of signs and symptoms of the patient's medical condition. The emergency medical dispatch system may use the caller response information to generate an emergency medical dispatch response by trained emergency responders. The information gathered from the caller responses may be used by the determinant value calculator to calculate a determinant value that can be communicated to the emergency responders. Additional details relating to emergency medical dispatch protocols and user interfaces to interact with the same can be found in the earlier referenced U.S. patents.

The emergency medical dispatch protocol user interface 200 may also provide one or more diagnostic tool launch inputs 206. As illustrated, one or more buttons may be provided on the user interface as diagnostic tool launch inputs 206. As will be appreciated by a person of ordinary skill, the diagnostic tool launch inputs 206 may comprise a component other than a button, including familiar user interface components such as a drop down menu, a drop down selection box, a list, a check box, and a radio button. The diagnostic tool launch inputs 206 enable the dispatcher to launch a particular diagnostic tool. Although the emergency medical dispatch protocol may automatically initiate a diagnostic tool based on dispatcher-entered input indicative of one or more responses of the caller, the diagnostic tool launch inputs 206 provide a way for the dispatcher to manually (i.e. any time, at the dispatcher's discretion) initiate a diagnostic tool. In FIG. 2, a pandemic diagnostic tool launch input 208 is provided. The pandemic diagnostic tool launch input 208 comprises a button on the emergency medical dispatch protocol user interface 200. The button may include, for example, an icon or a symbol for pandemic virus to indicate that the button is the pandemic diagnostic tool launch input 208, which manually initiates the pandemic diagnostic tool.

Figure 3:
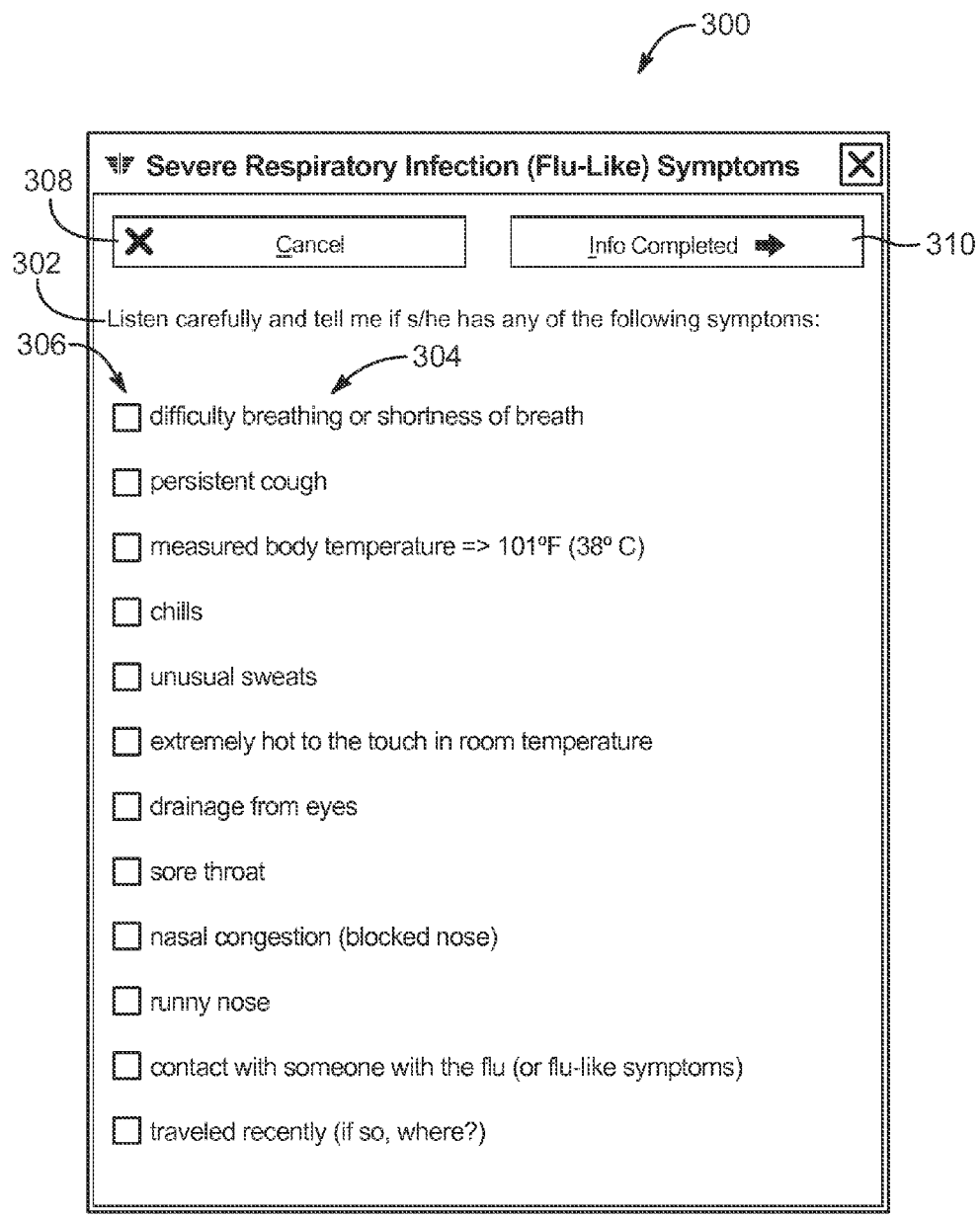
FIG. 3 illustrates a user interface of a pandemic diagnostic tool, according to one embodiment.

FIG. 3 is a user interface 300 of a pandemic diagnostic tool, according to one embodiment. The illustrated embodiment of the pandemic diagnostic tool may be configured to facilitate processing of a pandemic involving a severe respiratory infection, such as influenza (i.e., the "flu"). As can be appreciated, other embodiments may be configured to handle other forms of pandemic outbreaks involving other illnesses. The user interface 300 of the illustrated embodiment provides an instruction 302, symptoms 304, input fields 306, a "cancel" input 308, and an "info completed" input 310. These components of the user interface 300 may be presented to the user in a manner that provides a checklist. The user interface 300 aids a dispatcher in collecting information that can be used to identify patterns trends, and geographical clusters of symptoms of the flu and to facilitate effective and efficient utilization of scarce EMS, hospital, and community health care resources during a pandemic.

The instruction 302 is provided by the user interface 300 for the dispatcher to relay to the caller. The instruction 302 may be configured to be relayed by the dispatcher directly to the caller to, in effect, direct the caller. In another embodiment, the instruction 302 may be directed to the dispatcher, directing the dispatcher to, for example, perform an action or guide the caller in a particular manner. The instruction 302 may prepare the caller for additional instructions, questions, or prompts that may follow. For example, the instruction 302 may prepare the caller by providing, for example, "Listen carefully and tell me if s/he has any of the following symptoms." From this instruction, the caller is prompted to prepare to listen and observe and to indicate to the dispatcher which of the subsequently provided symptoms the patient may be manifesting.

The user interface 300 further provides a list of symptoms 304 that the dispatcher can relay to the caller over the telephone. The dispatcher can read the list of symptoms and after each symptom 304 allow the caller to respond, for example, "yes" or "no" as to whether the patient is manifesting one of the listed symptoms 304. Input fields 306 may be provided to enable the dispatcher to indicate to the diagnostic tool which of the symptoms 304 the caller reports the patient may be manifesting.

As previously indicated, the user interface 300 illustrated in FIG. 3 may be configured to facilitate processing of calls related to a pandemic outbreak of a severe respiratory infection, such as the flu. Accordingly, the user interface 300 may provide symptoms 304 related to severe respiratory infection, including but not limited to symptoms such as "difficulty breathing or shortness of breath," "persistent cough," "measured body temperature at or above 101 degrees Fahrenheit," "chills," "unusual sweats," "hot to the touch in room temperature," "drainage from eyes," "sore throat," "nasal congestion (blocked nose)," "runny nose," "contact with someone with flu (or flu-like symptoms)," and "traveled recently."

The input fields 306 of the illustrated user interface 300 are provided as check boxes. The dispatcher can easily click the check box input field 306 associated with a symptom 304 that the caller indicates the patient is manifesting. In essence, the illustrated user interface 300 presents a checklist of potential symptoms 304 that the dispatcher can quickly read and vocally relay to the caller over the telephone. The caller can in turn vocally relay which symptoms 304 from the list are being manifest by the patient. The dispatcher can utilize the check boxes 306 to quickly indicate which of the symptoms 304 the patient may have. As will be appreciated by a person of ordinary skill, the input fields 306 may comprise a component other than a check box, including familiar user interface components including but not limited to text fields, text boxes, menus, drop-down menus, drop-down selection boxes, lists, buttons, and radio buttons, or combinations thereof.

By providing a list of symptoms, and an input associated with each symptom in the list, the pandemic diagnostic tool facilitates a dispatcher uniformly and consistently gathering symptom information. A dispatcher utilizing the pandemic diagnostic tool can aid a caller to evaluate a definite set of symptoms of the pandemic illness. The checklist format substantially increases the likelihood that the dispatcher will address each symptom for each potential case of the pandemic illness. If a symptom is omitted from the gathered information, there can be reasonable confidence that the dispatcher and/or caller considered the symptom but the patient simply was not manifesting the omitted symptom. Moreover, presenting the list of symptoms ensures that the same description of the symptoms is being considered for each potential case. A particular symptom reported in one case can reasonably be compared to or measured against the same symptom in another case. Data from case to case will be uniform and consistent, meaning that the data provides in a definite manner whether a patient does or does not manifest a particular symptom from a known and definite set of symptoms.

The pandemic diagnostic tool may be configured to collect symptom information provided by the dispatcher via the input fields 306 for use in tracking pandemic outbreaks. The collected symptom information may be stored for processing or transferred for storage and/or processing. The collected data may be pre-processed, prior to transfer or storage, for example, by formatting, tagging with a mark-up language, filtering, or other processing. In another embodiment, the stored data may be substantially identical to the symptom information gathered by the dispatcher and provided to the diagnostic tool via the input fields 306.

The stored and/or transferred data (i.e. the symptom information) may be utilized, for example, to identify an increase in symptoms of the pandemic illness over a given time frame. The symptom information gathered from the dispatcher-entered input may be stored for analysis. Analyzing the data may include data mining, which may be described more particularly to include processing a collection of data to identify patterns and relationships within the collection of data through the use of advanced statistical methods. The analysis of the data may be delayed or may be real-time. A data analyzing module (e.g., third-party expert data-mining software) can track data gathered in the symptom information and/or by the emergency medical dispatch protocol to detect potential outbreaks within a geographic region so that alerts can be made to public health and governmental authorities. The data may enable tracking of the pandemic and predictive measures to forecast when the pandemic might hit a geographic area. The symptom information can also be passed to the CAD, and/or to the emergency responders. Providing the symptom information to the emergency responders can warn the responders if the patient is manifesting symptoms of the pandemic illness. Receiving advanced notice that the patient potentially has the pandemic illness allows the responders to take proper precautions to protect themselves from contracting the illness.

The specific symptoms 304 may change as a pandemic outbreak spreads and more information is known about the disease. Accordingly, the user interface 300 may be configured to be rapidly updated to provide current, accurate symptoms 304 for relay by the dispatcher to the caller. The protocol of the diagnostic tool can also be updated to reflect the most current information available on the illness. Updates to the user interface 300 and diagnostic tool protocol may be provided, for example, by download via ftp or http via the Internet. Furthermore, the pandemic diagnostic tool may be capable of being re-configured to handle different pandemic illnesses. For example, a pandemic diagnostic tool may be configured to be updated with a new set of symptoms 304 for a different disease (e.g., smallpox or Anthrax, instead of influenza). The user interface 300 presents the new set of symptoms, while the pandemic diagnostic tool may still perform the previously described gathering, processing, and/or storing functions to enable monitoring and tracking of the new disease.

An 'info completed' input 310 may be provided by the user interface 300 to indicate when all symptom information is entered and the entered information can be used (e.g., collected, mined, processed, etc.). After the dispatcher has entered input indicative of all the symptoms that the caller relays that the patient may be manifesting, the input may be collected and/or communicated by the dispatcher clicking on the info completed input 310. When info completed input 310 is received, the diagnostic tool may collect the symptom information provided through the input fields 306. The collected data (i.e. the symptom information) may be immediately processed, or stored for processing at a later time. The data may also be transmitted to a data analyzing module, potentially on another computer. The data may also be communicated to the emergency dispatch protocol, the CAD system and/or the emergency responders. In one embodiment the data may be passed to the emergency dispatch protocol, which then passes the data to the CAD system via a communication file. The emergency dispatch protocol may receive the data and use it when generating an emergency dispatch response. Moreover, the determinant value calculator may use the data to calculate a determinant value to generate an appropriate dispatch response and/or establish the priority of the emergency call. The CAD system may communicate the data to the emergency responders.

The user interface 300 may further provide a cancel input 308, which may be used by the dispatcher to halt progression of the diagnostic tool. The cancel input 308 in the illustrated embodiment may be a button. The dispatcher may have entered symptom information using the input fields 306, and for some reason determined that the information entered should not be considered by the tool (e.g., gathered, stored, mined, processed, etc.). For example, the caller may provide information to indicate the symptoms of the patient are clearly not resultant from infection with the pandemic illness. A dispatcher utilizing a pandemic tool configured for a pandemic flu outbreak may determine that a potential flu symptom, such as difficulty breathing, may in fact be the patient's chief complaint and not cause by a pandemic influenza virus. Accordingly, the dispatcher can click the cancel input 308 to terminate operation of the diagnostic tool without gathering any entered data.

In addition to collecting the symptom information provided via the input fields 306, the pandemic diagnostic tool may also make a determination as to whether the patient is likely infected with the illness of the pandemic outbreak. For example, the pandemic diagnostic tool may use the symptom information to make a determination whether the patient likely has a severe respiratory infection such as influenza.

If the pandemic diagnostic tool determines that the patient likely is infected with the pandemic illness, additional instructions may be provided to the dispatcher to guide the caller in taking precautions to protect herself/himself and in containing or quarantining the patient and the illness. In the illustrated embodiment, the pandemic diagnostic tool 122 provides the determination as to whether the patient is likely infected with the pandemic illness to the emergency dispatch protocol. The result of the determination may be incorporated into the traversal of the logic tree of the emergency dispatch protocol. For example, subsequent determinations as to how the emergency dispatch protocol proceeds along the logic tree of the protocol may be based, at least in part, upon the determination of the pandemic diagnostic tool. The emergency dispatch protocol may also receive the information. The emergency dispatch protocol may initiate a pandemic emergency dispatch protocol to further assist the dispatcher in processing the pandemic related call.

Figure 4:
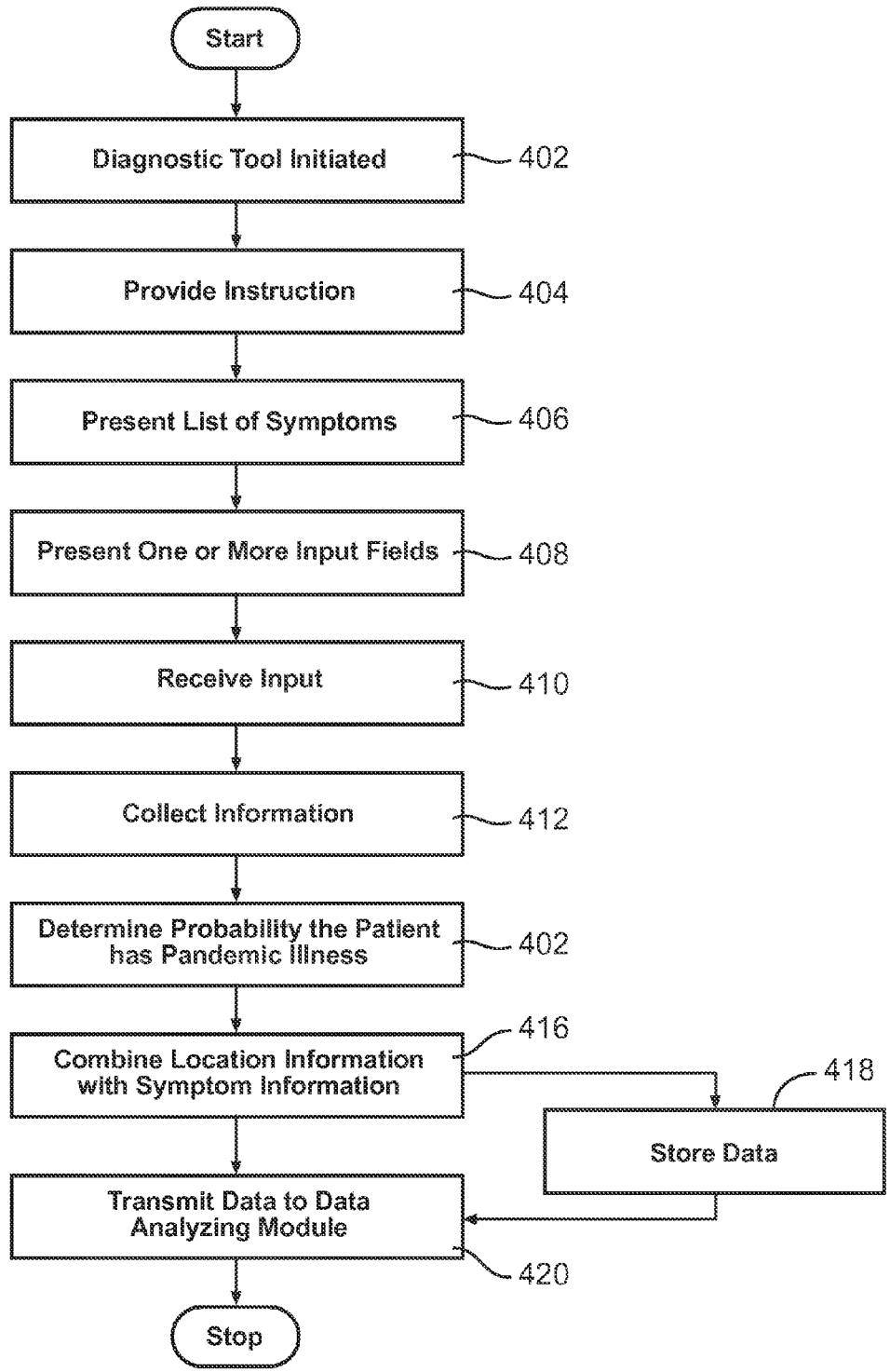
FIG. 4 is a flow diagram of a method for using a pandemic diagnostic tool to assist a dispatcher, according to one embodiment.

FIG. 4 is a flow diagram of a computer-implemented method to assist a dispatcher when communicating with a caller regarding a patient potentially having a pandemic illness, according to one embodiment. A pandemic diagnostic tool is initiated 402 on a dispatch center computer. The diagnostic tool may provide 404 one or more instructions via a diagnostic tool user interface. A list of symptoms of the pandemic illness may also be presented 406 on the diagnostic tool user interface. Presenting a list of symptoms facilitates ensuring that the set of symptoms considered from one emergency call to the next is consistent. One or more input fields are also presented 408 on the diagnostic tool user interface. The input fields may be associated with the list of signs or symptoms of the pandemic illness to enable a dispatcher to quickly indicate which of the signs or symptoms in the list the patient may be manifesting. The diagnostic tool user interface receives 410 the input via the input fields.

After the dispatcher has provided appropriate input for the emergency call, and the input has been received 410 by the user interface, the information is collected 412 by the diagnostic tool. Collecting 412 the information may include formatting symptom information into data having a uniform format. The diagnostic tool may use the collected information to determine 414 the probability that the patient has the pandemic illness. The collected information may also be combined 416 with location information gathered by the emergency dispatch protocol and/or the diagnostic tool. The location information specifies the location of the patient who is the subject of the emergency call. The combined data may optionally be stored 418 for later analyzing. The data may be stored locally on a dispatch center computer. The data, whether stored 418 or not, may be transmitted 420 to a data analyzing module. In other words, the data may be stored 418 first or may be directly transmitted for processing by the data analyzing module. The data analyzing module may analyze the data to identify geographical clusters of symptoms and/or to identify trends and patterns indicating the spread of the pandemic illness. The data analyzing module be local (at the dispatch center) or may be at a third-party.

A person of ordinary skill can appreciate that the determination and input may also be communicated to other components of the emergency medical dispatch system 100. Moreover, other data may be communicated as well. All data collected by the diagnostic tools 120 may be conveyed to the determinant value calculator 110, the reporting module 114, the CAD system 112, and/or trained emergency responders. The data may also be stored by the system 100. The data collected by the pandemic diagnostic tool 122 may be transmitted to a data analyzing module 126. The data, including the data collected by the pandemic diagnostic tool 122, may be combined with other data prior to being communicated to other components. For example, the data collected by the pandemic diagnostic tool 122 may be combined with location information collected by the emergency dispatch protocol.

The information gathered by the diagnostic tools 120 may be used to assist emergency responders prior to arrival. The diagnostic tools 120, including the pandemic diagnostic tool 122, greatly improve information collection and intervention for emergency medical response situations and will be an aid in saving lives.

While specific embodiments and applications of the disclosure have been illustrated and described, it is to be understood that the disclosure is not limited to the precise configuration and components disclosed herein. Various modifications, changes, and variations apparent to those of skill in the art may be made in the arrangement, operation, and details of the methods and systems of the disclosure without departing from the spirit and scope of the disclosure.

What is claimed is:

1. A computer-implemented method to assist a dispatcher when communicating with a caller via telephone regarding a medical emergency of a patient, comprising:
   a dispatch center computer system providing an emergency dispatch protocol to assist the dispatcher communicating with the caller via telephone regarding a medical emergency of a patient, the protocol presenting a plurality of interrogatories for the dispatcher to ask the caller to collect information regarding the medical emergency and generate an emergency medical dispatch response by emergency responders based on the collected information;
   the dispatch center computer system initiating a diagnostic tool on the dispatch center computer system, the diagnostic tool configured to aid the dispatcher in uniformly collecting information about symptoms of a pandemic illness in a uniform consistent manner;
   the diagnostic tool presenting to the dispatcher a user interface;
   the diagnostic tool providing an instruction via the user interface for the dispatcher to vocally relay to the caller over the telephone to guide the caller in identifying symptoms of the pandemic illness that the patient is manifesting;
   the diagnostic tool receiving dispatcher-entered input that is indicative of information about symptoms of a pandemic illness gathered and relayed by the caller, wherein the caller relays the symptom information to the dispatcher vocally over the telephone;
   the diagnostic tool collecting symptom information from the dispatcher-entered input and compiling the symptom information into data having a uniform format to be processed to monitor the spread of the pandemic illness; and
   the dispatch center computer system transmitting the collected symptom information to a data analyzing module that is configured to identify patterns and relationships within data received by the data analyzing module.

2. The computer-implemented method of claim 1, wherein the pandemic illness is a severe respiratory infection.

3. The computer-implemented method of claim 1, wherein the pandemic illness is influenza.

4. The computer-implemented method of claim 1, wherein the diagnostic tool on the dispatch center computer system transmits the collected symptom information to the processing module.

5. The computer-implemented method of claim 1, wherein the diagnostic tool collecting information from the dispatcher-entered input comprises transferring the collected information to the emergency dispatch protocol of the dispatch center computer system, and wherein the emergency dispatch protocol transmits the collected symptom information to the processing module.

6. The computer-implemented method of claim 5, further comprising the dispatch center computer transferring the collected information to a computer-aided dispatch (CAD) system.

7. The computer-implemented method of claim 6, further comprising the dispatch center combining location information collected by the emergency dispatch protocol with symptom information before transferring the symptom information to the CAD system.

8. The computer-implemented method of claim 1, further comprising the diagnostic tool making a determination whether the patient is likely suffering from the pandemic illness, wherein the determination is based on the dispatcher-entered input.

9. The computer-implemented method of claim 8, further comprising the dispatch center computer system determining a priority for the emergency medical dispatch response based on the diagnostic tool determining that the patient is likely suffering from severe respiratory infection.

10. The computer-implemented method of claim 9, wherein the dispatch center computer system determining the priority further comprises determining a determinant value.

11. The computer implemented method of claim 8, further comprising the diagnostic tool providing to the emergency medical dispatch protocol the results of the diagnostic tool determination whether the patient is likely suffering from the pandemic illness.

12. The computer-implemented method of claim 1, wherein the dispatch center computer system initiates the diagnostic tool based on dispatcher-entered input indicative of one or more responses of the caller to the interrogatories presented to the dispatcher by the protocol.

13. The computer-implemented method of claim 1, further comprising the dispatch center computer system presenting to the dispatcher an emergency medical dispatch protocol user interface having a diagnostic tool launch input to initiate the diagnostic tool, wherein the dispatch center computer system initiates the diagnostic tool in response to the diagnostic tool launch input.

14. The computer-implemented method of claim 1, wherein the diagnostic tool providing an instruction via the user interface includes providing an instruction that directs the caller to indicate to the dispatcher the symptoms of the pandemic illness that the patient is manifesting.

15. The computer-implemented method of claim 1, wherein the computer-implemented method further comprises the diagnostic tool providing one or more symptoms of the pandemic illness that the dispatcher can vocally relay to the caller to guide the caller's observations of the patient's symptoms.

16. The computer-implemented method of claim 15, wherein the diagnostic tool providing one or more symptoms to the dispatcher includes providing one or more symptoms from a group of symptoms consisting of: difficulty breathing or shortness of breath; persistent cough; measured body temperature at or above 101 degrees Fahrenheit; chills; unusual sweats; hot to the touch in room temperature; drainage from eyes; sore throat; nasal congestion (blocked nose); runny nose; contact with someone with flu (or flu-like symptoms); and traveled recently.

17. The computer-implemented method of claim 1, further comprising the diagnostic tool providing input fields on the user interface by which the dispatcher can enter input indicative of the symptoms of the pandemic illness that the caller indicates the patient is manifesting.

18. The computer-implemented method of claim 17, wherein the input fields comprise check boxes, wherein each check box is associated with a symptom of the pandemic illness, wherein the symptom associated with the pandemic illness is included in a list of symptoms presented by the user interface.

19. The computer implemented method of claim 1, further comprising the diagnostic tool providing on the user interface a completed input configured to indicate to the diagnostic tool to collect the dispatcher-entered input.

20. The computer implemented method of claim 19, further comprising the diagnostic tool determining whether the patient is likely suffering from the pandemic illness upon receiving the completed input.

21. A computer system for collecting information to identify geographical clusters of symptoms of a pandemic illness, the computer system comprising:
 a processor;
 an input device in electrical communication with the processor;
 an output device in electrical communication with the processor; and
 a memory in electrical communication with the processor, and having stored thereon:
 an emergency dispatch protocol configured to assist a dispatcher communicating with a caller via telephone regarding a medical emergency of a patient, wherein the emergency dispatch protocol provides a user interface to present a plurality of interrogatories for a dispatcher to ask a caller to generate an emergency dispatch response, wherein the emergency dispatch protocol receives geographical location information, which is transmitted to a data analyzing module that is configured to identify patterns and relationships within data received by the data analyzing module; and
 a diagnostic tool to assist the dispatcher in guiding the caller in a uniform manner to gather symptom information relating to symptoms of the pandemic illness that the patient may be manifesting; wherein the diagnostic tool is configured to
 present to the dispatcher a diagnostic tool user interface on an output device, including an instruction and a list of one or more symptoms for the dispatcher to vocally relay to the caller over the telephone to assist the caller in identifying symptoms of the pandemic illness the patient is manifesting,
 receive, via the input device and the diagnostic tool user interface, dispatcher-entered input indicative of caller-relayed information regarding the symptoms of the pandemic illness that the patient is manifesting, and
 collect symptom information from the dispatcher-entered input and compiling the symptom information into data having a uniform format that can be processed to monitor the spread of the pandemic illness, wherein the data is transmitted to the data analyzing module with the geographical location information to enable the data analyzing module to identify geographical clusters of symptoms of the pandemic illness.

22. The computer system of claim 21, further comprising a computer aided dispatch (CAD) system configured to manage dispatcher tools, including the emergency dispatch protocol, for processing emergency calls.

23. The computer system of claim 22, wherein the emergency dispatch protocol transfers symptom information collected by the diagnostic tool to the CAD system.

24. The computer system of claim 22, wherein the diagnostic tool transfers symptom information to the CAD system.

25. The computer system of claim 22, wherein the emergency dispatch protocol receives geographical location information from the CAD system.

26. The computer system of claim 22, wherein the geographical location information and the system information are combined together in a uniform data format and transferred to the CAD system, and wherein the CAD system is configured to transmit the data to the data analyzing module.

27. The computer system of claim 21, wherein the diagnostic tool determines whether the patient is likely suffering from the pandemic illness based on gathered symptom information.

28. The computer system of claim 27, the memory of the computer system further has stored thereon a determinant value calculator to calculate a determinant value that can be utilized to prioritize an emergency response, wherein the diagnostic tool is configured to provide to the determinant value calculator the results of determining whether the patient is likely suffering from severe respiratory infection.

29. The computer system of claim 21, wherein the emergency dispatch protocol initiates the diagnostic tool based on dispatcher-entered input indicative of one or more responses of the caller to the interrogatories presented to the dispatcher by the emergency dispatch protocol.

30. A computer system of claim 21, wherein the emergency dispatch protocol provides an input on the user interface to enable a dispatcher to manually initiate the diagnostic tool.

31. A computer-readable storage medium including computer-readable instruction code for a dispatch center computer performing a method to assist a dispatcher when communicating with a caller via telephone regarding a medical emergency of a patient, the method comprising:
 providing an emergency dispatch protocol to assist the dispatcher communicating with the caller via telephone regarding a medical emergency of a patient, the protocol presenting a plurality of interrogatories for the dispatcher to ask the caller to collect information regarding the medical emergency and generate an emergency medical dispatch response by emergency responders based on the collected information;
 initiating a diagnostic tool on the dispatch center computer, the diagnostic tool configured to aid the dispatcher in gathering information about symptoms of a pandemic illness in a uniform consistent manner;

the diagnostic tool presenting to the dispatcher a user interface;

the diagnostic tool providing an instruction via the user interface for the dispatcher to vocally relay to the caller over the telephone to guide the caller in identifying symptoms of the pandemic illness that the patient is manifesting;

the diagnostic tool collecting symptom information from the dispatcher-entered input and compiling the symptom information into data having a uniform format to be processed to monitor the spread of the pandemic illness; and the dispatch center computer system transmitting the collected symptom information to a data analyzing module that is configured to identify patterns and relationships within data received by the data analyzing module.

32. The computer-readable storage medium of claim 31, wherein the diagnostic tool is initiated based on dispatcher-entered input indicative of one or more responses of the caller to the interrogatories presented to the dispatcher by the emergency dispatch protocol.

33. The computer-readable storage medium of claim 31, wherein the method further comprises presenting to the dispatcher an emergency medical dispatch protocol user interface having a diagnostic tool launch input to initiate the diagnostic tool, wherein the diagnostic tool is initiated in response to the diagnostic tool launch input.

34. The computer-readable storage medium of claim 31, wherein the method further comprises the emergency dispatch protocol determining a priority for the emergency medical dispatch response based on the diagnostic tool determining that the patient is likely suffering the pandemic illness.

35. The computer-readable storage medium of claim 31, wherein the method further comprises the diagnostic tool providing input fields via the user interface by which the dispatcher can enter input indicative of caller-relayed information concerning the caller's observations of the patient's symptoms.

36. A computer system to assist a dispatcher when communicating with a caller via telephone regarding a medical emergency of a patient, the computer system comprising:
a processor;
an input device in electrical communication with the processor;
an output device in electrical communication with the processor; and
a memory in electrical communication with the processor, and having stored thereon:
an emergency dispatch protocol including a plurality of interrogatories for a dispatcher to ask a caller to generate an emergency medical dispatch response;
a diagnostic tool to assist the dispatcher in guiding the caller to obtain information that can be used by the diagnostic tool to diagnose whether the patient is likely suffering from a pandemic illness by performing a method of:
presenting to the dispatcher a user interface on the output device, including instructions for the dispatcher to vocally relay to the caller over the telephone to assist the caller in identifying symptoms that indicate the patient is likely suffering from the pandemic illness;
receiving dispatcher-entered input that is indicative of information about symptoms of a pandemic illness gathered and relayed by the caller, wherein the caller relays the information to the dispatcher vocally over the telephone;
collecting symptom information from the dispatcher-entered input and compiling the symptom information into data having a uniform format to be analyzed to monitor the spread of the pandemic illness; and
transmitting the collected symptom information to a data analyzing module that is configured to identify patterns and relationships within data received by the data analyzing module.

37. The computer system of claim 36, wherein the method of the diagnostic tool further comprises determining whether the patient is likely suffering from the pandemic illness, wherein the determination is based on the dispatcher-entered input.

38. The computer system of claim 37, wherein the method of the diagnostic tool further comprises providing to the emergency medical dispatch protocol the results of the determination whether the patient is likely suffering from the pandemic illness.

39. The computer system of claim 37, further comprising a determinant value calculator stored on the memory to calculate a determinant value that can be utilized to prioritize an emergency response, and wherein the method of the diagnostic tool further comprises providing to the determinant value calculator the results of determining whether the patient is likely suffering from the pandemic illness.

* * * * *